United States Patent [19]

Lynch

[11] Patent Number: 5,521,384

[45] Date of Patent: May 28, 1996

[54] FLOW CELL

[75] Inventor: Donald C. Lynch, Frederick, Md.

[73] Assignee: Perstorp Analytical, Inc., Silver Spring, Md.

[21] Appl. No.: 440,470

[22] Filed: May 12, 1995

[51] Int. Cl.$^6$ ................................................ G01N 21/05
[52] U.S. Cl. .................. 250/343; 250/910; 356/410; 356/440; 356/246
[58] Field of Search .................................. 250/343, 910; 356/410, 440, 246

[56] References Cited

U.S. PATENT DOCUMENTS 4,260,257  4/1981  Neeley et al. ........................... 356/246

5,046,854  9/1991  Weller et al. ........................... 356/440

*Primary Examiner*—Carolyn E. Fields
*Attorney, Agent, or Firm*—Lane, Aitken & McCann

[57] ABSTRACT

A flow cell for use in optical measuring systems particularly suited for use with liquid food products is provided. The flow cell is manufactured from a single unitary piece of synthetic resin which is transparent to light in the near infrared range. Because the flow cell is constructed from a single piece, the interior surface is continuous and the presence of undesirable cracks or crevices is avoided.

10 Claims, 4 Drawing Sheets ns in the

FLOW CELL

FIELD OF THE INVENTION

This invention relates to an improved flow cell for optical measuring systems and a method of manufacturing the same. The invention is particularly suited for use in connection with the infrared measurement of liquid dairy products and other liquid food products.

BACKGROUND OF THE INVENTION

Optical sensing is a common non-invasive manner to measure the various constituents which make-up food products. One often employed manner of optical sensing is performed using an infrared light source, fiber optic cable and photodetectors. Infrared light is passed through a food sample and light transmitted through the sample is measured and analyzed by photodetectors. The data generated by the photodetectors can provide an accurate measurement of a given sample's constituent make-up because each component has unique absorbance properties and thus a unique optical signature in the infrared range.

One application for this technology involves optical sensing in connection with the production and processing of dairy products. In the production of dairy products it is desirable to quantitatively measure various constituents of the product such as fat, water, solids and sugar content from a stream of flowing liquid. Measurement of these components involves passing the flowing liquid past light emitted from an infrared source and then measuring the light transmitted through the sample with photodetectors. The apparatus which provides a location to direct infrared light through a flowing sample stream is referred to as a flow cell. Light generated from an infrared source is transmitted through a fiber optic cable to a window area in the flow cell which is transparent to infrared light. Infrared light passes through the window area and then through the sample passing through the flow cell. Light that is not absorbed by the sample then passes through an opposite window area where it is received by a second fiber optic cable. The second cable transmits the incident light to a photodetector where the intensity of the transmitted light is measured. The various constituents of food products such as milk, salad dressing, cheese, and yogurt have unique absorbance spectra in the infrared range. Quantitative measurements of the constituents of the food products can be by carried out measuring the light transmitted through the sample at predetermined wavelengths in the near infrared range. Using a device as described herein, a food producer can continuously monitor the various levels of constituents in his product throughout the production phase.

In prior art systems, fiber optic cables transmitting infrared light are received in a flow cell by opposite cylindrical extensions positioned perpendicular to an axis parallel to the direction of flow of the sample. In the flow cells which are currently commercially available, the cylindrical extensions are made of polysulfone. Fiber optic cables are received in a tubular cavity which ends in a distal circular window area. In the prior art flow cells, the window areas are positioned at the end of extensions which radially extend from the sidewalls of the flow cell and into the conduit carrying the food product. The windows are positioned in this manner so that light only passes through a reduced sample section as compared to the diameter of the conduit. Such a reduced section is generally required because an adequate amount of infrared light cannot sufficiently penetrate a large distance through a sample so as to enable a photodetector to make accurate measurements. The optimal distance between the opposite windows in a flow cell is dependant on the product that will be measured.

Standard sanitary gaskets made of rubber are used at the interface between the conduits carrying liquid food products and the flow cells. These sanitary gaskets merit and receive close scrutiny because of the interest in keeping the food supply free from contamination. Any interface between component parts provides a location for the potential introduction of harmful contamination. Because of the concern with contamination, there is a voluntary approval program which certifies acceptable conduit system components such as gaskets for use in the dairy industry. Although flow cells used for optical measurements are not subjected to any specific government regulatory approval framework, the 3-A establishes voluntary guidelines governing the use of food conduits in the dairy industry. Many producers therefore require 3-A approval of all component parts which potentially could come into contact with a food supply including flow cells.

Standard operating practice in the dairy industry dictates that the conduits carrying food products and all the fittings used therein be thoroughly cleaned on a daily basis. Because flow cells are within the conduits and are in contact with the food products they must also be disassembled and cleaned after each use. Generally accepted design parameters for conduits designed to carry dairy products attempt to keep the interior surface of the conduits as smooth and even as possible. Any interruption of the interior surface, such as a crevice, provides a harbor for food products to accumulate, coagulate and spoil. The presence of coagulated milk or dairy products within a conduit provides a suitable environment for the growth of harmful bacteria which can contaminate an entire food supply passing through a particular conduit. Moreover, an accumulation can be abruptly released into the food product further contaminating the supply.

FIG. 1 depicts an exploded view in partial cross section of a flow cell which has been approved by the 3-A for dairy applications. The flow cell, generally designated by the reference numeral 9, is interposed between two conduits which carry a liquid food product and sealed in place using a pair of standard sanitary gaskets 10 and 11. Standard sanitary gaskets are also subject to 3-A approval. The gaskets are received in opposite circular recesses 12 and 13 located on opposite end walls of the tubular passageway. The flow cell depicted in FIG. 1 is a hollow cylinder having a diameter approximately equal to the diameter of the conduits 15 and 16 which respectively transfer the liquid food product to and from the sampling location. Located on sidewall 22 of the flow cell 9 are opposite circular openings. Opening 24 receives cylindrical member 26 and a second cylindrical member 28 is received in the same manner on the opposite side. Opposite cylindrical members 26 and 28 are made of polysulfone and transparent in the infrared spectrum. The members have central passages each which receives a fiber optic cable which in turn directs infrared light either to or from a window area. As illustrated in FIG. 1, member 26 has an interior passage 27 which ends at window area 29. When in use, infrared light passes through the window area and into the flowing sample. While a portion of the light is absorbed by the constituents in the sample, the remaining light is transmitted through the sample and falls upon the opposite window area 29a located on the end of cylindrical tube 28. The cylindrical members are positioned perpendicular to the direction of flow of the liquid food product to be measured as it passes through flow cell 9. As best shown in FIG. 2, at the base of each cylindrical member a seal is effected between surface 32 of the opening 24 and the exterior surface of the member. In the flow cell depicted in FIGS. 1 and 2 the seal employs an annular Teflon gasket 30 which is compressed into beveled circular surface 32. Exterior surface 34 of the Teflon gasket engages beveled surface 32 while the interior surface of the gasket simultaneously engages the exterior surface 55 of the cylindrical member to form a seal. Surrounding opening 24 and extending from the exterior sidewall of the flow cell is a hollow cylindrical extension element 38 which receives a spacer element 40. Referring back to FIG. 1, Teflon gasket 30 is compressed by rotation of a clamp 42 which has threads which engage opposite threads on extension element 38. As the components come together, surface 46 of spacer element 40 engages a washer element 48 which in turn engages Teflon gasket 30. At the same time, a flange 50 on cylinder 26 is also engaged by clamp 42 and is received in circular recess 58 on the opposite side of spacer 40. Compression of the gasket into the beveled surface forms a seal between the sidewall of the flow cell and sidewall 55 of cylindrical member 26. In addition to its function associated with forming the seal between the window and flow cell, spacer 40 aligns and retains the cylindrical tube in a position perpendicular to the direction of the sample flow. A first "O" ring gasket 52 is positioned between the clamp and the circular extension to prevent moisture from entering the cylindrical member. Fiber optic cable 61 is retained within the cylindrical member by a second clamp fastener 63 located adjacent to clamp 42. A second "O" ring gasket 65 is also provided to deter moisture from entering the assembly along the fiber optic cable.

It can be readily appreciated that the flow cell described herein and depicted in FIGS. 1 and 2 is a relatively complex assembly comprised of many parts. In addition to the problems and costs associated with the assembly and disassembly during the required cleaning procedures, the flow cell often exhibits a crevice in connection with the seal effected between the sidewalls of the flow cell and the cylindrical member. The presence of the crevice is related to the manner in which the components of the flow cell come together and can be exacerbated when the components are not precisely assembled. Even in instances where the components form true seal, there is often a narrow crevice or groove contiguous to the Teflon gasket at the interface between the cylindrical members and the interior wall of the flow cell. Despite efforts to minimize the incidence and size of such crevices, the occurrence of a small crevice is frequently manifested. The problems with the crevice are compounded because at its location adjacent to the cylindrical member, the crevice is further subjected to forces which result from the interruption of flow by the cylindrical member which extends into the flowing liquid. Existing crevices are thereby aggravated by the constant application of hydraulic forces. Crevices, or grooves are undesirable because food products can accumulate within them and a suitable environment is created for the growth of bacteria. It is evident from the foregoing description that prior art flow cells exhibit a number of disadvantages, particularly in dairy applications where it is necessary to frequently disassemble and clean all components in a conduit system.

OBJECT OF THE INVENTION

It is the object of the invention to provide an improved flow cell that avoids the potential formation of crevices next to the interface between the windows and the sidewalls of the flow cell. A further object of the invention is to provide an improved manner in which to retain a fiber optic cable within a flow cell assembly. Another object of the invention is to provide an extension that positions a window area in the center of a conduit which has a streamlined shape which minimizes the fluid forces acting upon the structure and provides sufficient area to incorporate a sample port at a location close to where the infrared light is directed through the sample. It is yet a further object of the invention to provide a less complex flow cell assembly which has a reduced number of component parts and thereby is both less expensive to produce, assemble, install, clean and maintain.

SUMMARY OF THE PRESENT INVENTION

The present invention is directed at an improved flow cell which is constructed from a single piece of synthetic resin and a method of manufacturing the same. To construct a flow cell according to the invention one begins by extruding polysulfone plastic into the shape of a rod having two semicircular or "D" shaped axial passages extending down its length. The rod is next divided into a series of disks which are then cut, milled, drilled and routed to form the improved flow cell. The improved flow cell has extensions extending from the interior sidewalls and formed from a single unitary piece of polysulfone. The flow cell has window areas which are also integral with and formed from the same piece of material as the extensions and sidewalls. A further feature of the invention is the fiber optic cable retention means which extend from the exterior sidewall of the tubular passageway. Because the material that the flow cell is flexible, the retention means which extend from the sidewall can be drawn together with conventional nut and bolt fasteners to frictionally engage and retain a fiber optic cable. The flow cell according to the invention dispenses with the need for multiple parts and, rather than attempting to minimize the incidence of crevices at the interface between the extensions and sidewall, it solves the problem altogether by forming the entire unit from a single piece of material. In a preferred embodiment of the invention, the sidewalls, windows and cable retaining means of the flow cell are constructed of polysulfone however the flow cell could be constructed of other materials which are transparent to infrared light. Since the flow cell of the invention is constructed from a single piece, many of the spacers, clamps and fastening devices present in the prior art flow cells are unnecessary. Compared to prior art flow cells, the flow cell according to the invention has a reduced axial dimension which allows the flow cell to be attached between opposing conduits in an improved manner. It is apparent that construction of the flow cell in the manner according to the invention, makes the numerous advantages recited above possible.

DETAILED DESCRIPTION OF THE INVENTION

Figure 1:
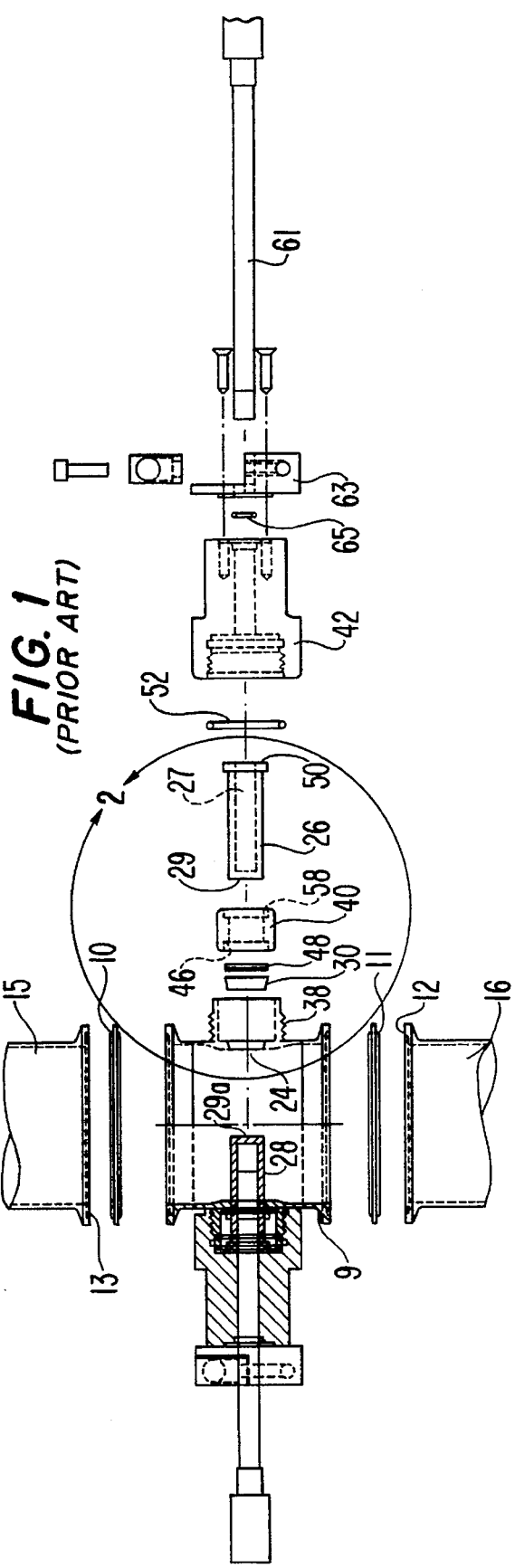
FIG. 1 is a partial sectional view of a prior art flow cell along an axis defined by the opposite windows with one side shown in an exploded view.
Figure 2:
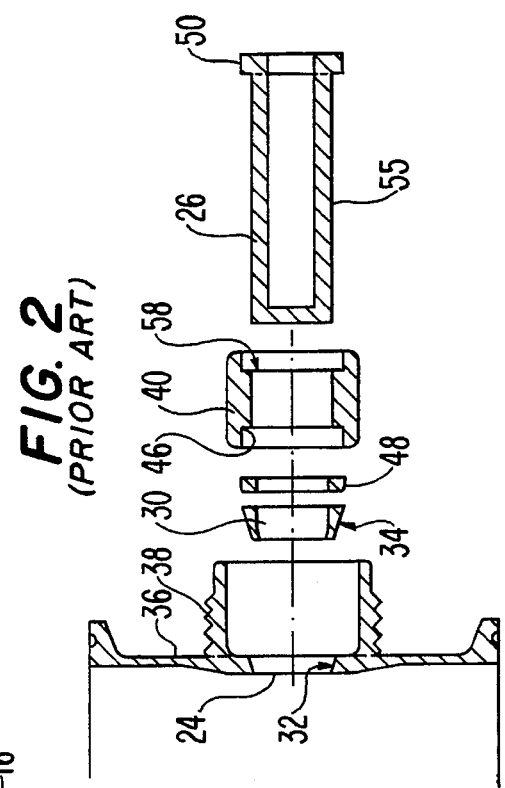
FIG. 2 is an enlarged sectional view of the portion of FIG. 1 within the circle 2.
Figure 3:
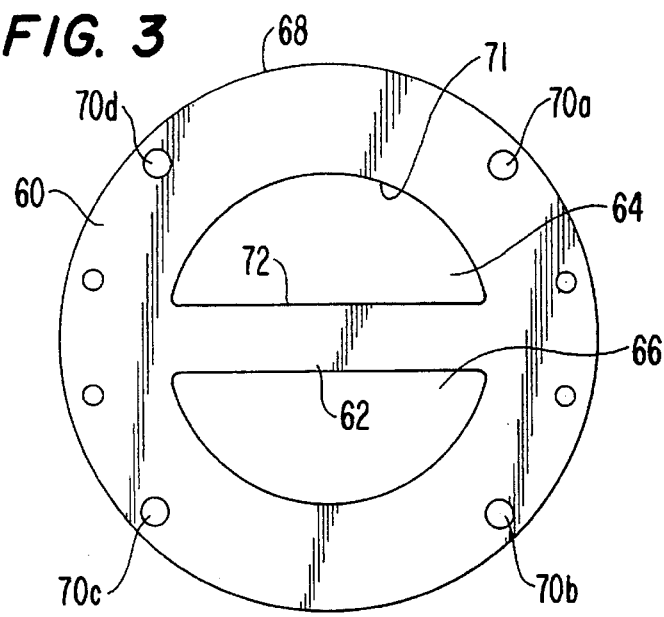
FIG. 3 is a top plan view in elevation of the extruded piece of plastic from which the flow cell of the invention is formed after a first step of the manufacturing process.

A flow cell according to the invention is formed by first extruding a blank made of polysulfone into a tube having a circular cross section and separated into two semicircular passages by a central bridge. Although polysulfone is the preferred material to use to construct the flow cell, it is contemplated that other food grade plastics which are transparent to infrared light such as polycarbonate or polyether sulfone would be acceptable. The tube is then cut into a series of disks, each having an axial dimension of approximately 1.5 inches. FIG. 3 depicts a top view of a cylindrical disk 60 which represents an early stage of the manufacturing process. Referring to FIG. 3, a central bridge 62 bisects and divides the disk to form two semicircular or "D" shaped passages, 64 and 66. Passage 64 is defined by an inner side wall 71 and the sidewall 72 of the central bridge.

Figure 4:
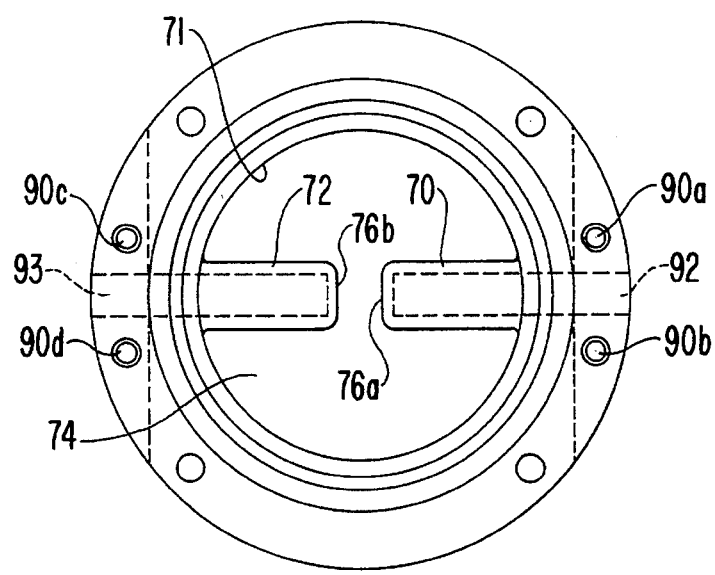
FIG. 4 is a side plan view in elevation showing the flow cell of the invention in an intermediate stage of the manufacturing process.

A further manufacturing step involves providing a series of through holes 70a, 70b, 70c and 70d which axially extend through the disk around the periphery. The through holes can receive conventional nut and bolt fasteners which are used to attach the flow cell to conduits which transfer liquid food products to and from the flow cell. As best shown in FIG. 4, a further step in the manufacture of the flow cell involves the removal of a rectangular shaped section of the central bridge 62 to form a pair of opposite extensions 70 and 72. Upon removal of the rectangular section, the D shaped passages are united to form a single central passage 74 where the liquid sample to be analyzed will flow. The section is removed to result in the extensions being positioned at an optimal distance apart so that there is a sufficient amount of light transmitted through the sample to make accurate measurements. The optimal distance between the extensions 70 and 72 is determined by the particular substance that is to be measured and therefore each particular product to be measured will have its own unique flow cell. The distance between the windows can range anywhere between 15 to 34 millimeters. Counter bore holes 92 and 93 are drilled into the opposite extensions 70 and 72 to form passages which receive the fiber optic cables. The extensions 70 and 72 serve to position window areas 76a and 76b, located on the distal ends of the extensions, a predetermined distance from each other.

Figure 5:
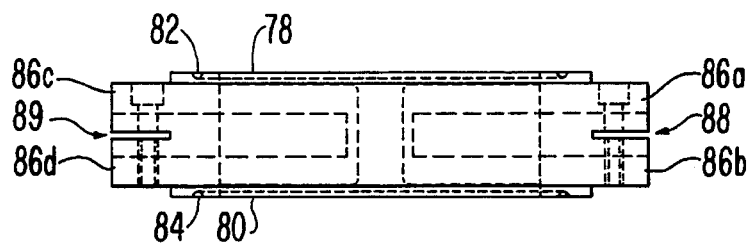
FIG. 5 is a side plan view in elevation of the flow cell according to the invention.

As FIG. 5 illustrates, both the top surface 78 and bottom surface 80 of the new flow cell are provided with annular recesses 82 and 84 which have semicircular profiles. The recesses are formed to receive standard sanitary gaskets. In a preferred embodiment of the invention, wing-like extensions 86a, 86b, 86c and 86d radially extend from opposite sides of the tubular passage. As shown in FIGS. 4 and 5, the extensions are segment shaped and formed from the same single piece of material. The wing-like extensions have a reduced axial dimension to provide for enhanced flexibility. Construction of the wing-like extensions first involves removing from both sides of the disk an annular region from the end walls. Removal of the annular region from the top and bottom of the flow cell results in a disk having an outer annular section which has a reduced axial dimension when compared to the maximum axial dimension of the flow cell. Reducing the axial dimension of this outer section contributes to the increased flexibility of the wing extensions which engage the fiber optic cables. The outer annular section is then provided with opposite flat bottomed grooves 88 and 89 to define the wing extensions 86a–86d. As best seen in FIG. 4, the grooves are parallel with each other and perpendicular to the extensions. FIG. 4 further shows additional through holes 90a, 90b, 90c, and 90d which are provided to extend through the wing extensions. The holes are employed in connection with the retention of the fiber optic cables. Because the flow cell is constructed of a flexible synthetic resin, the wafer-like wing extensions can be axially displaced to frictionally engage a fiber optic cable inserted between them and into bore holes 92 and 93. Fasteners are then inserted through holes 90a, 90b, 90c and 90d to retain the extensions in a flexed condition. Compression of the fiber optic cables by the wing extensions holds the cables in place.

Figure 6:
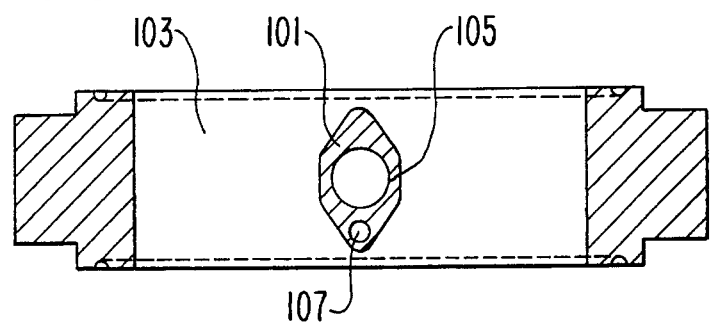
FIG. 6 is a side sectional view of the flow cell according to the invention.

After cutting the tube into disks, the extensions 70 and 72 have a flat planar surface facing the direction of flow. As best shown in FIG. 6, the extensions are next milled to form extensions having a diamond or hexagonal shape section when viewed along their respective axes to give the extension a streamlined profile. By forming the extensions from the same piece of material that makes up the sidewalls, the extensions can be formed in streamlined shapes, which was not practical in prior art flow cells. The hexagon shaped extensions promote laminar flow of the liquid, reduces the force acting upon the extension by the liquid flow and provide the space necessary to accommodate a sample port in close proximity to the measurement location. Although a streamlined shape such as a hexagon is preferred, the extension could be formed in other streamlined shapes and still retain the advantages recited above.

Constructed in the manner disclosed herein, the sidewalls, the extensions and window areas are formed from one single piece of material. Because the flow cells are formed from a unitary piece, there is no need for fittings to seal the extension means at the location where they extend from the flow cell sidewall. By providing a design that does not require fittings, the problem of crevices is effectively eliminated.

Figure 7:
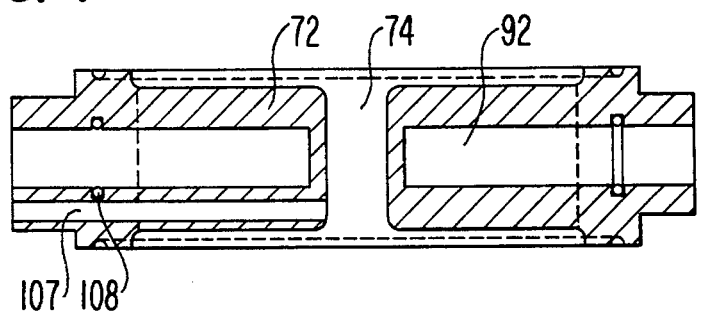
FIG. 7 is a second side sectional view of the flow cell according to the invention.

In a preferred embodiment of the invention, a second bore hole 107 is drilled in one of the extensions to form a tubular passage which serves as a sample port. As seen in FIGS. 6 and 7, the sample port extends all the way through the extension and provides access to the central passage area 74. Reference numeral 108 designates an "O" ring gasket positioned in a recess which serves a seal the end of the fiber optic cable within the tubular passage. Sealing the surface of the cable will prevent moisture from entering the assembly and interfering with the transmission of light through the window area.

In the prior art, samples were obtained by a conventional stop cock or spigot assemblies which were separately interposed within the conduit system. The sample port 107 within the extension allows a liquid sample to be taken in close proximity to the location where the infrared light is directed through the sample and the measurement is taken. Incorporation of a sample port with the flow cell also further reduces the number of components parts which make up the conduit system.

Figure 8:
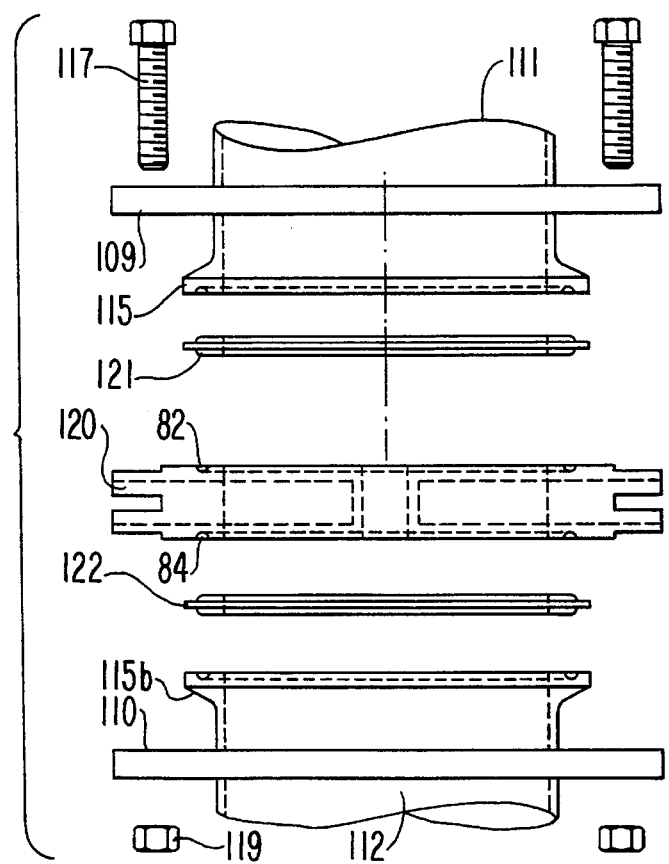
FIG. 8 is a side exploded view in elevation of the flow cell according to the invention shown in attachment within a conduit system.

The flow cell of the invention can be attached to conventional conduits in a variety of ways. Because of the reduced axial dimension and the absence of flange structures on the new flow cell, it is practical to attach the improved flow cell between opposite conduits using considerably less hardware. As seen in FIG. 8, the improved flow cell can be attached between two conduits using a pair of flat annular rings 109 and 110 which have openings which correspond to the through holes of the flow cell. Rings 109 and 110 are positioned behind flanges 115*a* and 115*b* which are located on the ends of conduits 111 and 112 respectively. Engaging the threads on bolt 117 with nut 119 draws the components of the fitting together and compresses the sanitary gaskets 121 and 122, located on either side of the flow cell, 120 to form seals.

Figure 9:
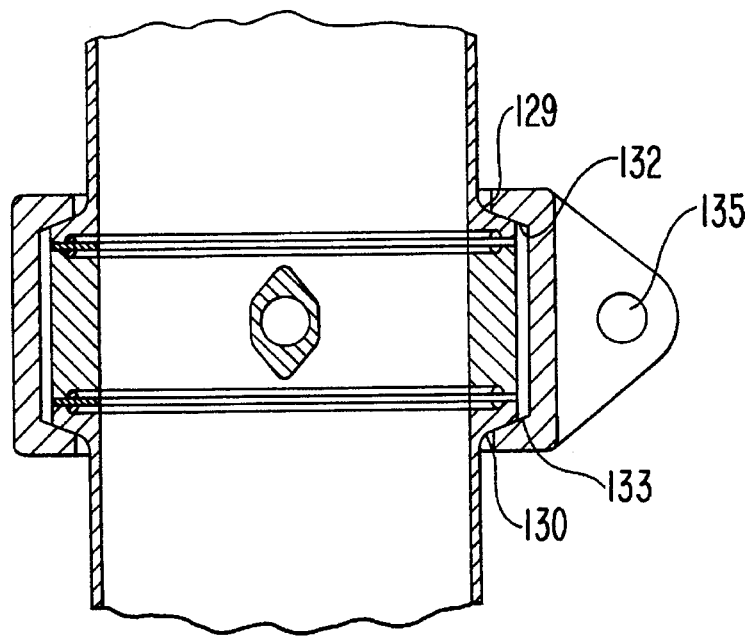
FIG. 9 is a side section view in elevation of an alternative manner in which to connect a flow cell constructed according to a second embodiment of the invention within a conduit system.
Figure 10:
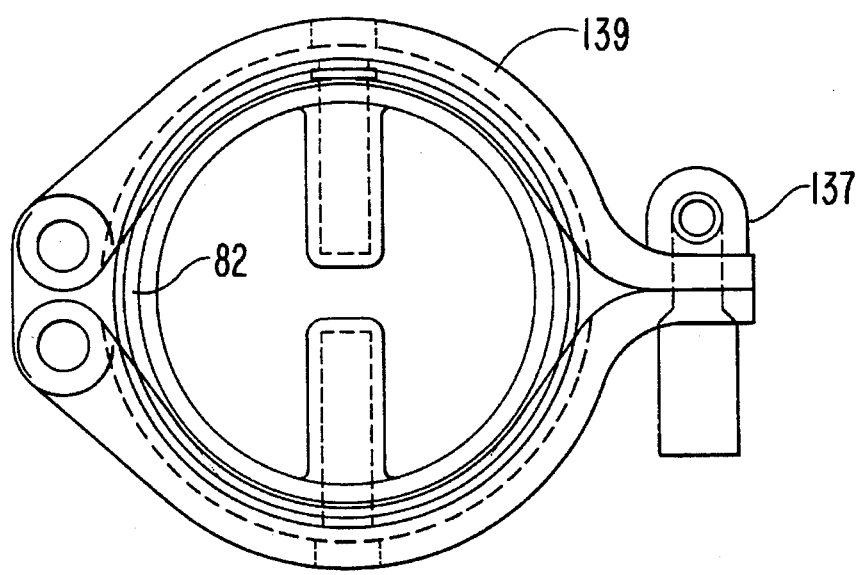
FIG. 10 is a top view of the sleeve clamp and flow cell as depicted in FIG. 9 with the upper conduit removed.

An alternative manner to connect the flow cell of the invention is depicted in FIGS. 9 and 10. The flow cell depicted in FIGS. 9 and 10 does not incorporate the wing extension features. As depicted in FIG. 9, a single sleeve clamp designed to be used with the invention simultaneously engages the flanges 129 and 130 with beveled surfaces 132 and 133. By tightening a fastener 137, the clamp 139 comes together and the beveled surfaces exert a force on the flanges drawing the conduits together. The flow cell is sandwiched between the conduit ends and sealed on either side with gaskets which are the same as those used in the alternative embodiment described above. The sleeve clamp further incorporates opposite openings (not shown) on its sidewalls to accommodate the fiber optic cables and cable retention means. Although multiple sleeve clamps have been used in conjunction with attaching prior art flow cells, the use of a single sleeve clamp is practical using the flow cell of the invention because the axial dimension of flow cell is significantly reduced. Furthermore, the simple design of new cell eliminates the need for spacers, large clamping structures, separate fiber optic cable retention means, and the flanges which are found on prior art flow cells. The presence of these structures would significantly interfere with use of a single sleeve clamp. Both embodiments of attachment differ from prior art flow cells because the improved flow cell does not have a flange structure on the ends of the tubular passage. The improved design allows attachment of the flow cell using less hardware and correspondingly takes less time to complete the task of assembly. Furthermore, the number of components which must be cleaned after use is reduced.

The above description is of a preferred embodiment of the invention and modification may be made thereto without departing from the spirit and scope of the invention which is defined in the appended claims.

We claim:

1. An improved measuring system for measurement of the constituent make-up of a liquid sample comprising a flow cell conduit means to cause a liquid sample to flow through said flow cell, said flow cell comprising a tubular passageway having sidewalls and opposite extensions, said sidewalls having an outer surface and an inner surface, said extensions radially extending inwardly from said inner surface and having distal ends which incorporate opposite window areas, said windows areas being positioned to allow infrared light to be transmitted through said flow cell perpendicular to an axis formed by said tubular passageway, said sidewalls, said extensions and said window areas comprising of single unitary integral piece of synthetic resin, said synthetic resin being transparent to infrared light in said window areas.

2. An in-line flow cell for use in an optical sensing system to measure the constituents of a flowing liquid sample comprising sidewalls defining a tubular passage and having an inner surface and an outer surface, a pair of opposite extensions each having an opposite window area positioned at the distal end of each said opposite extension, said opposite extensions extending inwardly into said tubular passage from said inner surface in a direction perpendicular to an axis defined by said tubular passage, said extensions having bore holes to receive fiber optic cables, said sidewalls, said extensions and said opposite windows areas being formed of a single integral piece of material, said window areas being transparent to infrared light.

3. A flow cell according to claim 2 further comprising fiber optic cable retention means formed from the same single integral piece of material which makes up said tubular passage, said fiber optic cable retention means comprising means to hold and retain fiber optic cables in said bore holes.

4. A flow cell according to claim 3 wherein said fiber optic cable retention means further comprise at least two wing-like extensions, said wing-like extensions being flexible so they can be axially displaced and means to secure said extensions in a displaced position wherein said wing-like extensions can frictionally engage and retain fiber optic cables.

5. A flow cell according to claim 3 wherein said fiber optic cable retention means further comprise wing-like extensions in the shape of segments.

6. The flow cell as recited in claim 2 wherein axial sections through said opposite extensions have streamlined profiles.

7. The flow cell as recited in claim 2 wherein said single integral piece of material is polysulfone.

8. The flow cell as recited in claim 2 further comprising a sample port defined through one of said extensions, said sample port comprising a tubular passage radially extending from the central passage of the flow cell to the exterior surface of the flow cell.

9. A method of manufacturing a flow cell comprising extruding a polysulfone blank into a rod shaped structure having a diameter of a predetermined size and a pair of axial "D" shaped passages separated by a central bridge section, separating the rod into a plurality of disk shaped sections each having opposite end walls and cylindrical sidewalls, removing a predetermined section of said central bridge section to form opposite extensions, counter boring through said extensions to form hollow cavities.

10. The method of manufacturing a flow cell as described in claim 9 further comprising shaping said extensions to have a streamlined profile.

* * * * *